United States Patent [19]

Peterson

[11] 4,402,216
[45] Sep. 6, 1983

[54] ERYTHROCYTE DEFORMABILITY MONITOR

[75] Inventor: David D. Peterson, Pleasanton, Calif.

[73] Assignee: Nuclepore Corporation, Pleasanton, Calif.

[21] Appl. No.: 298,195

[22] Filed: Aug. 31, 1981

[51] Int. Cl.³ .............................................. G01N 33/48
[52] U.S. Cl. ................................................. 73/61.4
[58] Field of Search .................... 73/61.4, 61 R, 64; 356/39, 42, 335; 210/927

[56] References Cited

U.S. PATENT DOCUMENTS 2,190,808  2/1940  Stover ................................. 73/61 R
3,709,614  1/1973  Hayakawa ....................... 356/335 X

FOREIGN PATENT DOCUMENTS 9318 10/1955 Fed. Rep. of Germany .......... 73/64

Primary Examiner—James J. Gill
Assistant Examiner—Joseph W. Roskos
Attorney, Agent, or Firm—Flehr, Hohbach, Test, Albritton & Herbert

[57] ABSTRACT

A method and device is provided for simply and rapidly measuring erythrocyte deformability by placing samples of blood on a set of porous membranes or a membrane strip with graded series of sharply defined pore sizes to determine the selective absorption thereon. Based on observation of the selective absorption on the membranes or membrane strip the deformability index of the erythrocytes may be determined.

11 Claims, 3 Drawing Figures

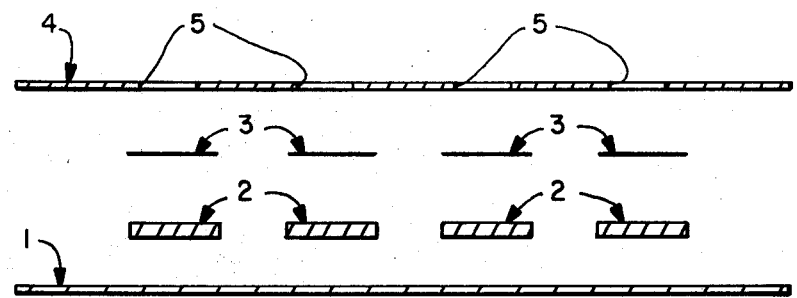
FIG.—1
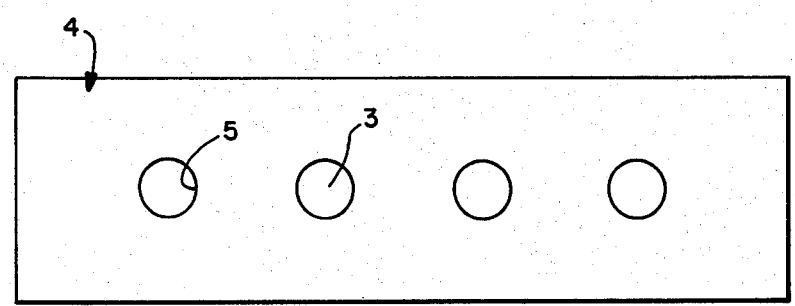
FIG.—2
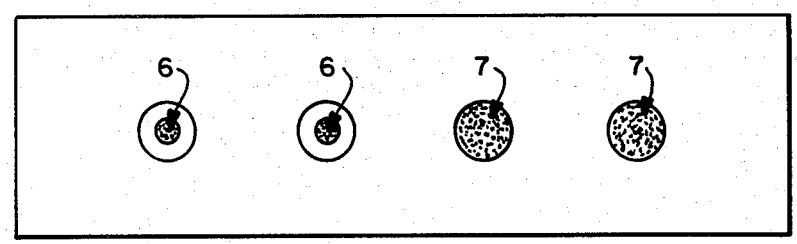
FIG.—3

ERYTHROCYTE DEFORMABILITY MONITOR

The present invention is drawn to a method and means for a rapid, convenient and simple clinical evaluation of erythrocyte (a red blood cell) deformability. The determination of cellular deformability permits descrimination between healthy and diseased human erythrocytes.

It is known that in order for healthy erythrocytes to pass through the microcirculatory capillary system within the body they need to undergo considerable deformation. Lessin et al. (Blood Cells 3 241-262 (1977)) disclose that normal human erythrocytes demonstrate a greater deformability than cells with the sickle cell trait, hereditary spherocytosis or sickle cell anemia. The method of measuring deformability of erythrocytes disclosed by Lessin et al. is to filter suspension of erythrocytes through a micro filter under a positive pressure cell filtration system and to measure the resistance of the suspension to flow across the micropore filter by pressure change induced by varying the flow rate. The system disclosed by Lessin et al. is complex, expensive, and time consuming.

Reid et al. (J. Clin. Pharm. 29, 855-858 (1976)) disclose the measurement of the deformability index of red blood cells in terms of volume of red blood cells filtered through a membrane filter per minute. The system disclosed by Reid et al. calls for the use of whole blood and the filtration must be induced by negative pressure to draw the blood through the membrane filter. The system is expensive in that a vacuum device is required, and is relatively time consuming and inconvenient, particularly since there may be a variation in pressure drop during the course of filtration which affects the accuracy of measurement. The system of Reid et al., therefore, requires constant attention to the suction device in order to attempt to maintain a relatively constant negative pressure.

It is therefore, an object of the present invention to provide a simple, rapid and convenient method for evaluating the deformability of healthy and diseased erythrocytes.

It is also the object of the present invention to provide a method and means to evaluate erythrocyte deformability by an index whose value is determined from the visual readout of the device provided by the present invention.

It is another object of the present invention to provide a means and method for conveniently and rapidly determining whether erythrocytes are normal or diseased, such method and means being particularly adapted for medical and clinical applications.

The human erythrocyte has a mean diameter of about 7.5 microns, however, it is known to pass easily through capillaries as small as 3 microns in diameter due to its ability to deform. This ability to deform allows an erythrocyte to squeeze through small capillaries in the body without hemolysis (cell wall rupture). According to the present invention, the deformability of an erythrocyte may be easily and rapidly determined by placing a sample of anticoagulated whole blood or a suspension of red blood cells onto a series of membranes having progressively decreasing pore sizes from about 10 microns to approximately 0.5 microns. Each membrane is backed by absorbent pads which draws/suspension through the membrane by capillary action. Depending on the deformability of the erythrocyte and on the size of the membrane pores, the erythrocyte will be either drawn through the membrane (positive absorption) or will remain on the membrane surface (negative absorption). Positive absorption is signaled by a complete disappearance of the erythrocyte-containing droplet from the top surface of the membrane. Negative absorption is indicated by some droplet residue, either wholly or partially, remaining on the surface of the membrane. Readout is made by observation of the positive or negative absorption at each spot. This readout should be carried out following a short-time interval after droplet em placement on the surface of each membrane.

Preferably a strip is provided which accommodates several membranes with various pore sizes which are selected so that normal red blood cells will not pass through the membrane having the smallest pore size. The deformability index, DI, is derived according to the following equation:

$$DI = N/M$$

Wherein N is the number of membranes showing positive desorption and M is the total number of membranes.

The invention is more particularly set forth below in the following embodiments, examples and figures, of which:

FIG. 1 is a diagram of the cross-section of a strip accommodating various sized membranes for use in accordance with the present invention.

FIG. 2 is a schematic top view of a strip accommodating various sized membranes according to the present invention.

FIG. 3 is a strip as shown in FIG. 2 showing the observable results of negative and positive absorption.

Referring to FIG. 1 there is shown a shematic side view of an erythrocyte deformability monitor (EDM) according to the present invention. The base 1 is a thin, hydrophobic material which supports the outer components of the EDM device and may be impervious to liquid penetration. On one surface of base 1 and in contact therewith a plurality of absorbent pads 2 which are used as backing to the membranes 3 to absorb liquid and thereby draw erythrocytes through the membranes. On the upper surface of each pad 2 is a membrane 3. The membranes 3 are each of a different mean pore size and are characterized by a high density of straight-through, capillary-shaped pores in a very thin polymeric film. Typically, the mean pore sizes in membranes 3 may vary between about 0.5 and 10 microns. The thickness of each membrane may be about 10 plus or minus one micron with the pore size in each membrane being plus or minus 5% of the stated calibrated mean value of the membrane. A particularly preferred class of sized membranes is disclosed in U.S. Pat. No. 3,303,085, the disclosure of which is incorporated herein by reference. The membranes and pads are held in place by label 4 which may be formed from a plastic film preferably clear, and may be bonded at various points by pressure sensitive adhesive, or by other means such as heat sealing, to the base 1. The bonding of label 4 to base 1 holds the membranes 3 and pads 2 in place. Access to each membrane is provided by a plurality of holes 5 in label 4. The individual pores which pass through the body of each membrane 3 have a randomly distributed angle of incidence between 0° and 30°. The pores are also randomly distributed over the surface of each membrane.

Referring to FIG. 2 there is shown a diagrammatic top view of an assembled EDM according to the present invention. There is shown label 4 with a plurality of holes 5 through which are exposed a plurality of membranes 3.

Referring to FIG. 3 there is shown the observable results of positive and negative absorption on the EDM shown in FIG. 2. After a sample droplet of a suspension containing erythrocytes is placed in the center of each membrane 3, one of two possible observable results are attained. In FIG. 3, the spots 6 indicate negative absorption wherein the erthrocytes remain in place on the membrane where they are originally placed. These spots 6 are erythrocytes which have not passed through the membranes 3. The larger spots 7, however, are indications of positive absorption wherein the deformability and the force of capillary action have caused the erythrocytes to pass through the membrane. The enlarged spot is caused by the darkness in the area soaked with the absorbed blood. In recording the results of a test on such EDM spots, such as 6, are recorded as negative and spots, such as 7, are recorded as positive.

The method of monitoring the deformability of erythrocytes provided by the instant invention includes the step of selecting a series of approximately 4 of 5 membranes having nominal mean pore sizes ranging from about 0.5 to 10 microns, preferably from about 2 microns to about 8 microns. The membranes are selected to give a different EDM response between healthy and diseased selected so that there be at least one positive and at least one negative reading on a test of healthy erythrocytes. This may be determined by selecting a set of membranes and screening it with a set of standard reference red blood cells which may be provided by Blood Bank Quality (BBQA) reference. An example of screening is shown below in Table 1 for a set of membranes having mean pore sizes of 7.5, 6.4, 4.6 and 2.6 microns.

Alternatively, a continuous membrane strip may be utilized with a gradation of pore size from one end of the strip to the other. The deformability would then be measurable as a function of the length of the strip through which blood cells pass.

TABLE 1

ERYTHROCYTE DEFORMABILITY
OF BBQA REFERENCE RED BLOOD CELLS

| BLOOD CELL TYPE | SIGNAL ON MEMBRANE | | | | DI (N (+)/4) |
|---|---|---|---|---|---|
| | 7.5 | 6.4 | 4.6 | 2.6 | |
| $A_1$ (3%) | + | + | + | − | 0.75 |
| $A_2$ (3%) | + | + | + | − | 0.75 |
| B (3%) | + | + | + | + | 1.00 |
| OD(Rho)-Neg. (3%) | + | + | + | − | 0.75 |
| OD(Rho)-Pos. (3%) | + | + | + | − | 0.75 |
| Coombs Pos. (5%) | + | + | + | − | 0.75 |
| A/S (30%) | + | + | − | − | 0.50 |
| A/A (30%) | + | + | + | − | 0.75 |

The series of membranes additionally must be able to differentiate between healthy and diseased red blood cells. Table 2 below shows a typical response for an EDM which consists of 5 membranes having normal pore sizes of 1, 2, 3, 5 and 8 microns.

TABLE 2

READINGS ON EDM FOR
SAMPLE OF HEALTHY (AA)
SICKLE CELL (SS) RED BLOOD CELLS

| RBC TYPE | Membrane Nominal Pore Size (Microns) | | | | |
|---|---|---|---|---|---|
| | 1 | 2 | 3 | 5 | 8 |
| AA | − | − | + | + | + |
| SS | − | − | − | + | + |

$DI_{AA} = 0.60$
$DI_{SS} = 0.40$

As shown above, the healthy blood cells pass through the 3, 5 and 8 micron membranes; whereas, the sickle cell diseased blood cells pass only through the 5 and 8 micron membranes. The calculated DI values in this case are 0.60 and 0.40, respectively, for healthy and diseased sickle cell blood.

The test on the EDM is performed by first preparing suspensions of red blood cells, and placing a droplet of each sample in the central region of each membrane on an EDM. Anticoagulated whole blood may be used in placed of prepared blood suspensions. It is preferred that the EDM be pre-wetted with a saline solution to ensure a more rapid and complete absorption process. A particular advantage of the present invention is that no external apparatus for producing positive or negative pressure is required to force or draw the red blood cells through the membrane. The blood sample is drawn through the membrane by the natural capillary forces exerted by the membrane and the absorbent pad backing. The two possible readings on an EDM are shown in FIG. 3 as described hereinabove. The proper selection of the range of pore sizes will always result in different DI values for healthy and diseased red blood cells.

It has been found that the sensitivity of the test performed according to the present invention is independent of hematocrit (the red blood cell concentration in suspension). Table 3 below indicates readings taken on membranes having nominal pore sizes of 1, 2, 3, 5 and 8 microns. Suspensions of healthy red blood cells were used having hematocrit values ranging from 1% to 47% as shown. For the hematocrit values, the identical DI value of 0.60 was obtained. However, since the test requires the observation of an enlarged spot on the membrane, there is a practical limitation on the hematocrit value. The positive readings taken on the 1% hematocrit samples are very faint, therefore, it is preferred that suspensions prepared for use in conjunction with the test have hematocrit values of above 1%, and preferably above about 5%.

TABLE 3

READINGS ON EDM FOR SAMPLES OF HEALTHY
RED BLOOD CELLS HAVING DIFFERENT
HEMATOCRIT VALUES

| Hematocrit Value (%) | Membrane Nominal Pore Size (Microns) | | | | |
|---|---|---|---|---|---|
| | 1 | 2 | 3 | 5 | 8 |
| 47 | − | − | + | + | + |
| 33 | − | − | + | + | + |
| 20 | − | − | + | + | + |
| 10 | − | − | + | + | + |
| 7.5 | − | − | + | + | + |
| 1 | − | − | (+) | (+) | (+) |

Note:
(+) indicates at 1% hematocrit that positive absorption occurs, but visibility is faint.
DI = 0.60 for all hematocrit values in Table 2.

Provided that a reasonable selection of a range of membranes having nominal pore sizes in the preferred range of about 1 micron to about 8 microns is selected for the design of the EDM, the sensitivity of the EDM is not particularly affected by design. Readings on EDM's of three different designs are shown below in Table 4 using examples of healthy (AA) and sickle cell (SS) red blood cells. The first EDM consists of 5 membranes having nominal pore sizes of 2.76, 3.5, 4.6, 6.0 and 7.5 microns. The second design EDM consists of 4 membranes having nominal pore sizes of 0.86, 1.74, 2.76 and 4.6 microns. The third design EDM consists of 5 membranes having nominal pore sizes of 0.86, 1.74, 2.76, 4.6 and 7.5 microns. In all three designs, the healthy cells and sickle cells are differentiated as indicated in Table 4 by their DI values. However, although the first design differentiates between healthy and sickle cell, the EDM results in all positive readings for healthy cells. As discussed hereinabove, it is preferred that at least one negative result be shown for a healthy blood cell. The reason for this is that the showing of at least one negative reading confirms that the healthy blood is satisfactory for testing, and also allows for screening of certain blood diseases which show higher DI values than healthy blood, such as microcytosis.

TABLE 4

READINGS ON EDM's OF 3 DIFFERENT DESIGNS USING SAMPLES OF HEALTHY (AA) AND SICKLE CELL (SS) RED BLOOD CELLS

| RBC TYPE | Membrane Nominal Pore Size (Microns) | | | | | | | DI |
|---|---|---|---|---|---|---|---|---|
| | 0.86 | 1.74 | 2.76 | 3.5 | 4.6 | 6.0 | 7.5 | |
| AA | | | + | + | + | + | + | 1.00 |
| SS | | | − | − | + | + | + | 0.60 |
| AA | − | − | + | + | | | | 0.50 |
| SS | − | − | − | + | | | | 0.25 |
| AA | − | − | + | | + | | + | 0.60 |
| SS | − | − | − | | + | | + | 0.40 |

What is claimed is:

1. A device for monitoring erythrocyte deformability comprising a plurality of membranes characterized by high density, straight-through, capillary-shaped pores, the mean pore size of each said membrane being in the range of about 0.50 microns and about 10 microns, each said membrane having a different nominal mean pore size from the others; each said membrane having absorbent material in contact with one surface thereof.

2. A device according to claim 1 wherein the thickness of each said membrane is from about 8 microns to about 12 microns and the surface to surface angular distribution of said pores within each said membrane is from 0° to about 30°.

3. A device according to claim 2 wherein said absorbent material is supported by a base member.

4. A device according to claim 3 further comprising a sealing member opposing and having points of adhesion to said base member thereby accommodating said membranes and absorbent material between said base material and said sealing member; said sealing member having a plurality of openings each corresponding to one of said membranes and each correspondingly exposing a substantial area of one of said membranes.

5. A device according to claim 4 wherein said mean pore size of each membrane is in the range of about 2 micron to about 8 microns.

6. A device according to claim 5 comprising five membranes having mean pore sizes of 1, 2, 3, 5 and 8 microns, respectively.

7. A method for evaluating the deformability of human erythrocytes comprising the steps of placing a suspension containing erythrocytes on a plurality of membranes, each said membrane characterized by a high density of straight-through, capillary shaped pores, each said membrane having a mean pore size of from about 0.5 micron to about 10 microns, each said membrane having a different nominal mean pore size from the others, each said membrane having an absorbent material on the opposite surface thereof, and determining for each said membrane whether the erythrocytes in said suspension are either substantially passed through said membrane onto said absorbent material or substantially retained on the surface of each said membrane.

8. A method according to claim 7 wherein the thickness of each said membrane is from about 8 microns to about 12 microns and the surface to surface angular distribution of said pores within each said membrane is from 0° to about 30°.

9. A method according to claim 8 wherein said absorbent material is supported by a base member.

10. A method according to claim 9 wherein said mean pore size of each membrane is in the range of from about 1 micron to about 8 microns.

11. A method according to claim 10 wherein said suspension is placed on five membranes having mean pore sizes of 1, 2, 3, 5 and 8 microns, respectively.

* * * * *